US006251591B1

(12) United States Patent
Wu et al.

(10) Patent No.: US 6,251,591 B1
(45) Date of Patent: *Jun. 26, 2001

(54) QUANTITATIVE METHOD FOR DETECTING NUCLEOTIDE CONCENTRATION

(75) Inventors: Yuan Min Wu; Eileen Xiao-Feng Nie, both of Thornhill (CA)

(73) Assignee: Lorne Park Research, Inc., Toronto (CA)

(*) Notice: Subject to any disclaimer, the term of this patent is extended or adjusted under 35 U.S.C. 154(b) by 0 days.

This patent is subject to a terminal disclaimer.

(21) Appl. No.: 09/083,837

(22) Filed: May 22, 1998

(Under 37 CFR 1.47)

Related U.S. Application Data

(63) Continuation-in-part of application No. 08/807,901, filed on Feb. 27, 1997, and a continuation-in-part of application No. 08/870,370, filed on Jun. 6, 1997, now Pat. No. 6,060,242, and a continuation-in-part of application No. 08/886,280, filed on Jul. 1, 1997, now Pat. No. 5,846,729.

(51) Int. Cl.[7] ............................... C12Q 1/68; C12P 19/34

(52) U.S. Cl. ............................................... 435/6; 435/91.1

(58) Field of Search ............................... 435/6, 91.2, 91.1

(56) References Cited

U.S. PATENT DOCUMENTS

| | | |
|---|---|---|
| 4,220,450 | 9/1980 | Maggio . |
| 4,469,863 | 9/1984 | Ts'o et al. . |
| 4,787,963 | 11/1988 | MacConnell . |
| 4,963,477 | 10/1990 | Tehen . |
| 5,100,775 | 3/1992 | Smyczek et al. . |
| 5,142,047 | 8/1992 | Summerton et al. . |
| 5,166,315 | 11/1992 | Summerton et al. . |
| 5,166,330 | 11/1992 | Engels et al. . |
| 5,217,592 | 6/1993 | Jones . |
| 5,217,866 | 6/1993 | Summerton et al. . |
| 5,223,618 | 6/1993 | Cook et al. . |
| 5,310,650 | 5/1994 | McMahon et al. . |
| 5,332,659 | 7/1994 | Kidwell . |
| 5,405,938 | 4/1995 | Summerton et al. . |
| 5,470,974 | 11/1995 | Summerton et al. . |
| 5,501,949 | 3/1996 | Marshall . |
| 5,503,980 | 4/1996 | Cantor . |
| 5,521,063 | 5/1996 | Summerton et al. . |
| 5,538,848 | 7/1996 | Livak et al. . |
| 5,539,082 | 7/1996 | Nielsen et al. . |
| 5,541,307 | 7/1996 | Cook et al. . |
| 5,587,469 | 12/1996 | Cook et al. . |
| 5,594,138 | 1/1997 | Dykstra et al. . |
| 5,602,240 | 2/1997 | De Mesmacker et al. . |
| 5,610,289 | 3/1997 | Cook et al. . |
| 5,618,704 | 4/1997 | Sanghvi et al. . |
| 5,623,065 | 4/1997 | Cook et al. . |
| 5,632,957 | 5/1997 | Heller et al. . |
| 5,674,698 | 10/1997 | Zarling et al. . |
| 5,677,437 | 10/1997 | Teng et al. . |
| 5,747,247 | 5/1998 | Kowalczykowski et al. . |
| 5,824,557 | 10/1998 | Burke et al. . |
| 5,846,729 | * 12/1998 | Wu et al. ................................. 435/6 |
| 6,060,242 | * 5/2000 | Nie et al. ................................. 435/6 |

FOREIGN PATENT DOCUMENTS

| | | |
|---|---|---|
| 0 232 967 | 8/1987 | (EP) . |
| 0411186 | 2/1991 | (EP) ............................... C12Q/1/68 |
| 0 512 334 | 11/1992 | (EP) . |
| 0 599 337 | 6/1994 | (EP) . |
| 0 781 853 | 7/1997 | (EP) . |
| 92 18650 | 10/1992 | (WO) . |
| 93 24652 | 12/1993 | (WO) . |
| WO 94/12665 | 6/1994 | (WO) . |
| 94 25477 | 11/1994 | (WO) . |
| WO 96/34983 | 11/1996 | (WO) . |
| 97 12995 | 4/1997 | (WO) . |
| WO98/38334 | 9/1998 | (WO) ............................... C12Q/1/68 |

OTHER PUBLICATIONS

Perry–O'Keefe et al., "Peptide Nucleic Acid Pre–Gel Hybridization: An Alternative to Southern Hybridization," 93 Proc. Natl. Acad. Sci. USA 14670 (Dec. 1996).

Smulevitch et al., "Enhancement of Stand Invasion by Oligonucleotides Through Manipulation of Backbone Charge," 14 Nature Biotechnology 1700 (Dec. 1996) (disclosed in Landsdorp, "Close Encounters of the PNA Kind," 14 Nature Biotechnology 1653 (Dec. 1996)).

Lansdorp, "Close Encounters of the PNA Kind," 14 Nature Biotechnology 1653 (Dec. 1996).

Egholm et al., "PNA Hybridizes to Complementary Oligonucleotides Obeying the Watson–Crick Hydrogen–Bonding Rules," 365 Nature 566 (1993).

Tomac et al., "Ionic Effects on the Stability and Conformation of Peptide Nucleic Acid Complexes," 118 J.Am. Chem.Soc. 5544 (1996).

Coghlan, "One–step DNA test in a tube," New Scientist, p. 21 (Nov. 5, 1994).

"PNA Oligomers as Hybridization Probes," vol. 1, Issue 2 of PerSeptive Biosystems Magazine, 1995.

(List continued on next page.)

*Primary Examiner*—W. Gary Jones
*Assistant Examiner*—Jehanne Souaya
(74) *Attorney, Agent, or Firm*—Caesar, Rivise, Bernstein, Cohen & Pokotilow, Ltd.

(57) ABSTRACT

The invention provides a method for rapidly, economically and efficiently determining the concentration of a target nucleobase-containing sequence in a fluid medium using laser induced fluorescence of antisense probes. When hybridization complexes and unhybridized probes are separated prior to detection, the fluorescent intensity of the test medium is proportional to the concentration of the target sequence. When hybridization complexes and unhybridized probes are not separated prior to detection, the fluorescent intensity of the test medium is inversely proportional to the concentration of the target sequence. The method can be used to determine the concentration of a contaminant in a sample as a part of a system of quality control.

32 Claims, 4 Drawing Sheets

OTHER PUBLICATIONS

Heppell–Parton, "Gene Mapping by Fluorescence in Situ Hybridization," pp. 350–54, in *Molecular Biology and Biotechnology: A Comprehensive Desk Reference* (Myers, ed. 1995).

Rawls, "Optimistic About Antisense," 75(22) Chem. Eng. News 35, 39 (Jun. 2, 1997).

Matthews et al., "Analytical Strategies for the Use of DNA Probes," 169 Analytical Biochemistry 1 (1988).

Carlsson C. et al., "Screening for Genetic Mutations," Nature, 380:207, Mar, 1996.

Jensen et al., "Kinetics for Hybridization of Peptide Nucleic Acids (PNA) with DNA and RNA Studied with the BiAcore Technique," 36(16) Biochem. 5072 (Apr. 1997).

Grunstein et al., "Colony Hybridization: A Method for the Isolation of Cloned DNAs that Contain a Specific Gene," Proc. Nat'l Acad. Sci., 72(10):3961–3965, 1975.

Meinkoth et al. "Hybridization of Nucleic Acids Immobilized on Solid Supports," Analytical Biochemistry, 138:267, 1984.

Thomas, "Hybridization of Denatured RNA and Small DNA Fragments Transferred to Nitrocellulose," Proc. Nat'l Acad. Aci. 77(9):5201–5205, 1980.

Wetmur, Biopolymers, 14:2517–2524, 1975.

Chang et al., Biopolymers, 13:1847–1858, 1974.

Zhang et al., "Single–base mutational analysis of cancer and genetic diseases using membrane bound modified oligonucleotides," 19(14) Nucleic Acids Research 3929–3933 (Jul. 25, 1991).

R. Hogrefe et al., Nucleic Acids Research, 1993, vol. 21:2031–2039.

Miller P.S. et al.—"Oligotymidylate Analogues Having Stereoregular, Alternating Methylphosphonate/Phosphodiester Backbones", *Journal of Biological Chemistry* (Microfilms), vol. 255, No. 20, Oct. 25, 1980 (1980–10–25), pp. 9659–9665, XP002059491.

Cardullo et al., "Detection of nucleic acid hybridization by nonradiative fluorescence resonance energy transfer," Proceedings of the National Academy of Sciences of the USA, vol. 85, No. 23 pp. 8790–8794, Dec. 1988.

Cooper et al., "Analysis of fluorescent energy transfer in duplex and branched DNA molecules," Biochemistry, vol. 29, pp. 9261–9268, 1990.

\* cited by examiner

```
                       SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
        (A) LENGTH: 150 bases
        (B) TYPE: nucleotide
        (C) STRANDEDNESS: double-stranded
        (D) TOPOLOGY: linear (ii) MOLECULE TYPE: genomic DNA (xi) SEQUENCE DESCRIPTION: SEQ ID NO:1:

AACACCAGCT CCTCTCCCCA GCCAAAGAAG AAACCACTGG ATGGAGAATA TTTCACCCTT       60

CAGATCCGTG GGCGTGAGCG CTTCGAGATG TTCCGAGAGC TGAATGAGGC CTTGGAACTC      120

AAGGATGCCC AGGCTGGGAA GGAGCCAGGG                                       150

(2) INFORMATION FOR SEQ ID NO:2:

(i) SEQUENCE CHARACTERISTICS:
        (A) LENGTH: 18 bases
        (B) TYPE: nucleotide
        (C) STRANDEDNESS: single-stranded
        (D) TOPOLOGY: linear (ix) FEATURE:
        (D) OTHER INFORMATION: nucleotide with four methylphosphonate
            substitutions along its backbone (xi) SEQUENCE DESCRIPTION: SEQ ID NO:2:

CCTCATTCAG CTCTCGGA                                                     18
```

QUANTITATIVE METHOD FOR DETECTING NUCLEOTIDE CONCENTRATION

CROSS-REFERENCE TO RELATED APPLICATION

This application is a continuation-in-part of our earlier patent applications, U.S. patent application Ser. Nos. 08/807,901, 08/870,370 now U.S. Pat No. 6,060,242, U.S. patent application Ser. No. 08/886,280 now U.S. Pat. No. 5,846,729, respectively filed Feb. 27, 1997, Jun. 6, 1997, and Jul. 1, 1997.

BACKGROUND OF THE INVENTION

1. Field of Invention

The invention relates to a method for detecting the concentration of a nucleobase-containing sequence in a sample. In particular, the invention relates to a method for detecting such a concentration using laser-induced fluorescent spectroscopy.

2. Description of Related Art

A popular method for detecting the concentration of nucleic acids in a sample employs ultraviolet spectroscopy to monitor the absorption of the sample at 260 nm. The bases of nucleic acids are chromophores having an ultraviolet radiation absorption maximum at about 260 nm. Thus, the amount of ultraviolet radiation absorbed at 260 nm is an indication of the concentration of nucleic acids in a sample.

However, this method for detecting nucleic acid concentration does not discriminate between different nucleic acid segments in the sample. The method merely provides information regarding the total amount of all nucleic acids in the sample. This can be particularly undesirable when the method is being used to determine the amount of a specific nucleic acid sequence in a sample that inadvertently contains unknown quantities of contaminating nucleic acid sequences.

Antisense probes have been used to obtain qualitative information regarding target nucleobase-containing sequences. See, e.g., U.S. Pat. No. 5,166,330 to Engels et al., U.S. Pat. No. 4,469,863 to Ts'o et al., U.S. Pat. No. 5,539,082 to Nielsen et al. and U.S. Pat. No. 5,503,980 to Cantor, Perry-O'Keefe et al., "Peptide Nucleic Acid Pre-Gel Hybridization: An Alternative to Southern Hybridization," 93 Proc. Natl. Acad. Sci. USA 14670 (December 1996), and Smulevitch et al., "Enhancement of Strand Invasion by Oligonucleotides Through Manipulation of Backbone Charge, " 14 Nature Biotechnology 1700 (December 1996) (disclosed in Landsdorp, "Close Encounters of the PNA Kind," 14 Nature Biotechnology 1653 (December 1996)).

Many types of sample analyses, including certain of the aforementioned antisense probe type assays, rely upon the fluorescent properties of a marker. See, e.g., U.S. Pat. No. 5,594,138 to Dykstra et al., U.S. Pat. No. 4,963,477 to Tchen, U.S. Pat. No. 5,538,848 to Livak et al., U.S. Pat. No. 4,220,450 to Maggio, U.S. Pat. No. 5,332,659 to Kidwell, and U.S. Pat. No. 5,674,698 to Zarling et al., and K. H. Andy Choo, Ed., "In Situ Hybridization Protocols," Chapters 2 and 4 (Humana Press, Totowa, N.J., 1994).

Fluorescence occurs when a molecule excited by light of one wavelength returns to the ground state by emitting light of a longer wavelength. The exciting and emitted light, being of different wavelengths, can be separated from one another using optical filters, a camera or a CCD. Fluorescence has been used to visualize certain molecules (and hence structures) by light microscopy for many years, and is also used in other analytical techniques, such as flow cytometry. Further, the emission of fluorescence showing different colors can be detected by a human eye, a camera, a charge coupled device (CCD) or a photomultiplier.

Until the present invention, however, it has not been possible to rapidly and specifically test for the concentration of a particular nucleotide sequence in solution using a method which does not destroy the sample, is less hazardous to laboratory personnel than radiation based assays, does not require the cost and delay of separating unhybridized probes from hybridization complexes, does not require the provision of quenching agents, does not require the provision of enzymes, does not require the provision of multiple interactive reporting moieties on, or in the vicinity of, each probe, does not require the provision of up-converting labels, and is readily automated.

All references and prior patent applications cited herein are incorporated herein by reference in their entireties.

SUMMARY OF THE INVENTION

The invention addresses at least the foregoing deficiencies in the art in providing a method for determining a concentration of at least one single stranded or double stranded nucleobase-containing target sequence in a fluid medium, said method comprising:

adding to said fluid medium antisense probes capable of forming hybridization complexes with said at least one nucleobase-containing target sequence;

separating unhybridized antisense probes from said hybridization complexes to form a test medium;

irradiating said test medium with a laser beam having a wavelength which excites fluorescent markers in said hybridization complexes and causes said fluorescent markers to emit fluorescent light;

measuring an intensity of said emitted fluorescent light; and comparing said measured intensity with a reference intensity to determine a concentration of said at least one target sequence in said fluid medium, wherein said measured intensity is proportional to said concentration, and wherein said method other than said separating step is entirely conducted without binding said antisense probes, said at least one nucleobase-containing target sequence or said hybridization complexes to a solid support or gel.

The invention also provides a method for determining a concentration of at least one single stranded or double stranded nucleobase-containing target sequence in a fluid medium, said method comprising:

adding to said fluid medium antisense probes capable of forming a hybridization complex with said at least one nucleobase-containing target sequence;

irradiating said fluid medium with a laser beam having a wavelength which excites fluorescent markers in said hybridization complex and causes said fluorescent markers to emit fluorescent light;

measuring an intensity of said emitted fluorescent light; and comparing said measured intensity with a reference intensity to detect whether said fluid medium contains said at least one target sequence, wherein said measured intensity is inversely proportional to said concentration, and said method is conducted without separating unhybridized probes from hybridization complexes prior to said signal detecting, and without providing a signal quenching agent on said antisense probes or on said at least one nucleobase-containing target sequence.

The invention thus provides methods for rapidly, economically and efficiently determining the concentration of a target nucleobase-containing in a sample using laser induced fluorescence of antisense probes. The methods can be used, e.g., to determine the concentration of a contaminant in a sample as a part of a system of quality control.

The methods can be conducted without separating unhybridized probes from the hybridization complexes prior to signal detecting, without providing a signal quenching agent on, or in the vicinity of, the probe or the nucleobase-containing sequence, without the use of enzymes, and without the use of up-converting labels.

BRIEF DESCRIPTION OF THE DRAWINGS

The invention will be described in conjunction with the following drawings in which like reference numerals designate like elements and wherein.

DEFINITIONS

Figure 1:
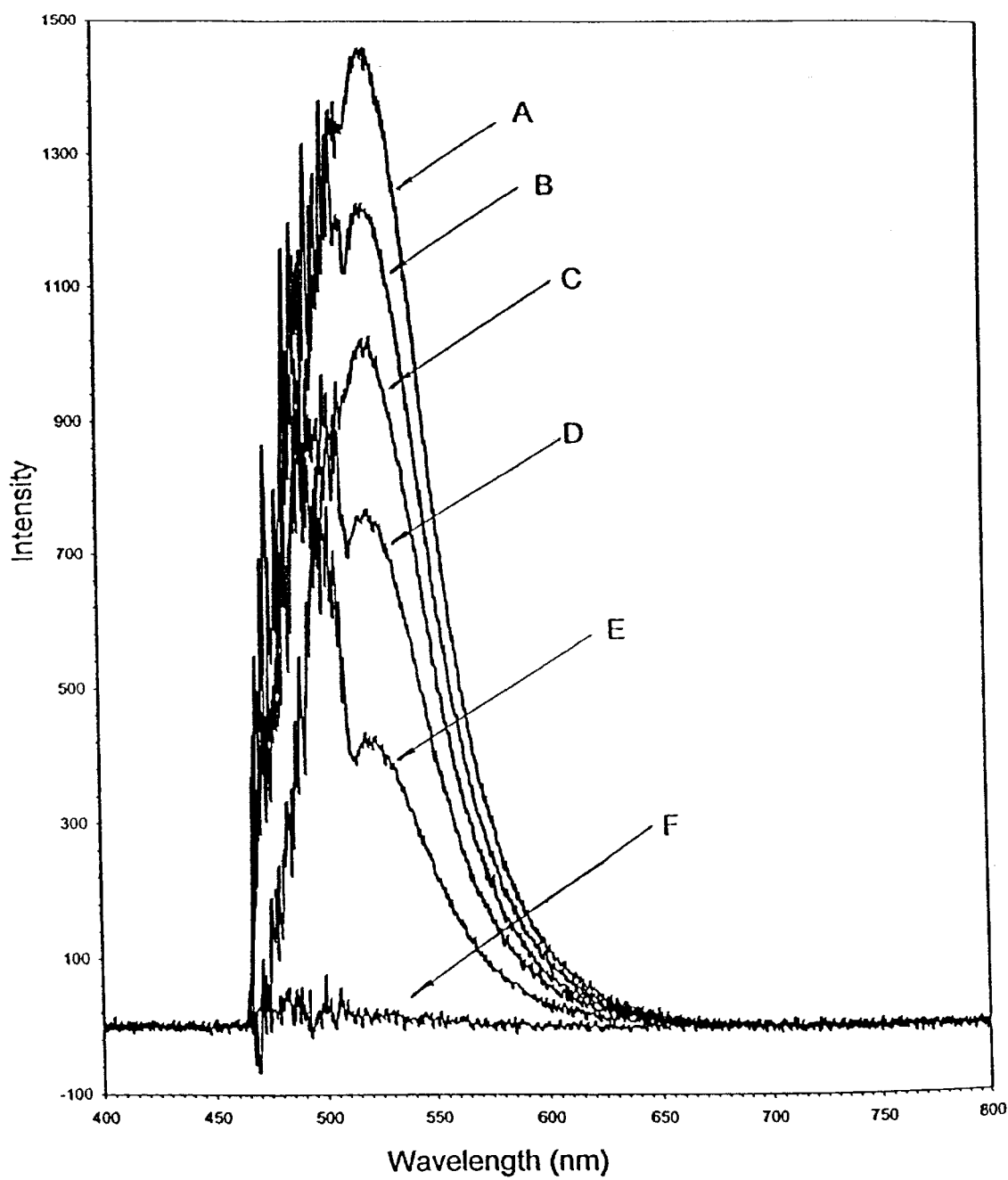
FIG. 1 shows the fluorescent spectra produced by a series of samples having increasing concentrations of a target nucleotide sequence.

Although the terminology employed herein generally conforms to conventional usage, the following definitions are provided to remove any doubt as to the meaning of selected terminology employed to help define the limits of the invention.

The expression "nucleobase-containing sequence" as used herein encompasses, e.g., DNA, RNA, modified nucleic acid sequences and PNA. The term is intended to encompass all molecules capable of specifically hybridizing via base pairing to complementary (or partially complementary) segments of DNA and/or RNA.

The expression "antisense probes" as used herein includes any nucleobase-containing sequence capable of specifically binding to another nucleobase-containing sequence having a base sequence complementary to the base sequence of the probe. The antisense probes of the invention can be complementary to either strand of dsDNA, for example.

DETAILED DESCRIPTION OF PREFERRED EMBODIMENTS

The method of the invention can be used to determine the concentration of a nucleobase-containing sequence in a fluid sample. The sample need not be a fluid initially, but if it is, e.g., a solid, it should be processed into a fluid form (e.g., a liquid or gaseous mixture) as an initial step in the method of concentration determination.

The method of the invention employs antisense probes to determine the concentration of a target nucleobase-containing sequence. Antisense probes having neutral backbones, such as PNA probes, are preferred, and anionic antisense probes of reduced negative charge are most preferred. The sensitivity of the invention appears to be most pronounced for DNA/RNA analog probes having reduced charge anionic backbones, such as methylphosphonate oligonucleotides. Probes having uncharged backbones, such as PNA and methylene methyl amino oligonucleotides, also appear to outperform native (i.e., phosphodiester) oligonucleotides as probes.

Preferred anionic probes have reduced negative charge due to the substitution of at least one, and preferably less than all negatively charged phosphate groups of each probe with a neutral group. Preferably, about half of the phosphate groups of the probe are substituted with neutral groups, more preferably about one-quarter of the phosphate groups of the probe are substituted with neutral groups.

It is preferred that the neutral group substituted for the native phosphate group be a methylphosphonate group; however other substituents are within the scope of the invention, including aminoethyl phosphonates, hydroxymethyl phosphonates, methylphosphonothioates, s-methyl phosphorothioates, phosphoramidites, and the like. Suitable methods for making such backbone substitutions are known in the art.

The probe can be homogeneously or heterogeneously substituted with neutral substituents. In homogeneous substitution schemes, only one type of backbone modification would be made to the probe. For example, in homogeneous substitution, the only modifications to the probe might be the substitution of methylphosphonate groups for phosphate groups, whereas in heterogeneous substitution, the probe could comprise a segment of PNA linked to a segment of methylphosphonated DNA.

Probe sequences having any length from 8 to 20 bases are preferred since this is the range within which the smallest unique DNA/RNA sequences of prokaryotes and eukaryotes are found. Probes of 12 to 18 bases are particularly preferred since this is the length of the smallest unique sequences in the human genome. However, a plurality of shorter probes can be used to determine the concentration of a nucleotide sequence having a plurality of non-unique target sequences therein, which combine to uniquely identify the nucleotide sequence.

At least the probes of the invention comprising PNA are able to form triplex complexes with dsDNA and duplex complexes with RNA or ssDNA. Such probes are also able to form triplex complexes wherein a first probe binds with RNA or ssDNA and a second ssDNA strand binds with the resulting duplex complex. See, e.g., Egholm et al., "PNA Hybridizes to Complementary Oligonucleotides Obeying the Watson-Crick Hydrogen-Bonding Rules," 365 Nature 566 (1993), and Tomac et al., "Ionic Effects on the Stability and Conformation of Peptide Nucleic Acid Complexes," 118 J. Am. Chem. Soc. 5544 (1996).

In the probes according to the invention, the bases attached to the backbone are primarily naturally occurring nucleobases attached at the position required by probe manufacture. Alternatively, the bases may be non-naturally occurring nucleobases (nucleobase analogs), other base-binding moieties, aromatic moieties, (C1–C4) alkanoyls, hydroxyls or even hydrogens. It will be understood that the term nucleobase includes nucleobases bearing removable protecting groups. Furthermore, at least one base on the backbone can be replaced with, or substituted with, a DNA intercalator, a reporter ligand such as, for example, a fluorophore, radio label, spin label, hapten, or a protein-recognizing ligand such as biotin. Preferred detectable labels include a radioisotope, a stable isotope, an enzyme, a fluorescent chemical, a luminescent chemical, a chromatic chemical, a metal, an electric charge, or a spatial structure.

In particularly preferred embodiments, the probe comprises an antisense sequence covalently bonded to a fluorescent marker, which fluoresces when irradiated with a laser. Preferred fluorescent markers include biotin, rhodamine and fluorescein.

In embodiments of the invention wherein unhybridized probe is separated from probe/target hybridization complexes, the fluorescent intensity of the hybridization solution is proportional to the concentration of the target sequence.

In embodiments of the invention wherein unhybridized probe is not separated from hybridization complexes prior to measuring fluorescence, the fluorescent intensity is inversely proportional to the concentration of the target sequence. That is, there is a quenching effect associated with hybridization of the probe and target sequence. The quenching effect varies with the marker selected. This effect enables the method of the invention to detect hybridization without employing a quenching agent on the probe (to quench unhybridized probe signal) or on the target sequence (to quench hybridized probe signal), as required by, e.g., Livak et al. and Maggio, supra.

Unlike Kidwell, supra, the instant invention does not require a plurality of electronically interacting fluorophores on each probe, because the fluorescent intensity quenching effect detected by the instant invention is not the same as the emission wavelength shift detected in Kidwell, which is caused by intramolecular excimer formation between adjacent fluorophores. The quenching effect of the instant invention is apparent with only one fluorophore per probe (although a plurality of fluorophores per probe are contemplated for certain embodiments).

In certain embodiments, the fluorescent marker is provided at the 5' terminal of the probe with a short linker. The position of the marker within the probe does not appear to be particularly significant.

Probes are added to a fluid (e.g., liquid) medium suspected of containing at least one nucleobase-containing sequence, and/or a mutant version of the at least one sequence. The medium can be any conventional medium known to be suitable for preserving nucleobase-containing sequences, such as nucleotides. See, e.g., Sambrook et al., "Molecular Cloning: A Lab Manual," 2d (1989). For example, the medium can be a liquid comprising nucleotides, water, buffers and surfactants.

The nucleotides in the medium can be obtained from clinical samples by any conventional method, including an automated method. Examples of such methods are summarized in, e.g., Sambrook et al., Vol. 2, pp. 9.16–9.19 and 7.6 to 7.7. An example of an automated nucleic acid purifying apparatus is the BioRobot 9600 manufactured by Quiagen (Chatsworth, Calif., USA).

The isolated nucleotides are added to the liquid medium and denatured prior to being detected. Preferably, the denaturation is conducted at about 90° C. to about 100°0C. for about 30 seconds to about 5 hours in the presence of PNA probe.

Preferably, probes are added to the liquid medium in a concentration 0.05 to 100 times the expected concentration of the nucleobase-containing sequence to be detected. This expected concentration can be determined theoretically or empirically, using the conventional 260 nm UV test as a guide.

Hybridization between complementary bases occurs under a wide variety of conditions having variations in temperature, salt concentration, electrostatic strength, and buffer composition. Examples of these conditions and methods for applying them are known in the art. See, e.g., Perry-O'Keefe et al., Egholm et al., Tomac et al., Sambrook et al., Vol. 2 pp. 9.47–9.55 and the Pre-Gel Hybridization Technique taught in Vol. 4, No. 3 of PerSeptive Biosystems Magazine.

It is preferred that hybridization complexes be formed at a temperature of about 4° C. to about 75° C. for about 2 minutes to about 24 hours. It is particularly preferred to conduct denaturing for no more than 60 minutes in the presence of PNA probe, after which the temperature is passively cooled to room temperature without quenching.

It is possible to facilitate hybridization in solution by using certain reagents. Preferred examples of these reagents include single stranded binding proteins such as Rec A protein, T4 gene 32 protein, E. coli single stranded binding protein, major or minor nucleic acid groove binding proteins, divalent ions, polyvalent ions, and intercalating substances such as ethidium bromide, actinomycin D, psoralen, and angelicin.

The preferred markers for use in the invention are fluorophores. As will be appreciated by the skilled artisan, the wavelength preferably selected to induce fluorescence of the fluorescent marker is known in the art as the "excitation maximum," i.e., that wavelength which is absorbed by a molecule and excites that molecule to a higher electronic state. When the marker molecule passes from the higher to a lower electronic state, the molecule emits a type of visible radiation, i.e., fluorescence, at a wavelength referred to as the "emission maximum." It is at least this fluorescence that is detected in the present invention. The detectable signal emitted by the compound can be detected using techniques known in the art, for example by observation with the human eye, using electronic means for detecting a generated wavelength (e.g., cameras and CCDs), and the like. Advantageously, the wavelength of fluorescence is sufficiently removed from that of the exciting light to allow good separation of the two wavelengths by optical filters. Contrary to the teachings of Zarling et al., supra, the present invention is sufficiently sensitive to obtain good fluorescence data with down-converting labels.

The excitation wavelength is selected (by routine experimentation and/or conventional knowledge) to correspond to this excitation maximum for the marker being used, and is preferably 200 to 1000 nm. For example, when the marker is fluoroscein, the preferred wavelength of excitation is about 488 nm. Fluorescent dyes are preferably selected to have an emission wavelength of 200 to 1000 nm.

In preferred embodiments, an argon ion laser is used to irradiate the marker with light having a wavelength in a range of 400 to 520 nm, and fluorescent emission is detected in a range of 500 to 750 nm.

An apparatus for performing the inventive method can comprise a liquid medium container for containing the liquid medium; a laser for irradiating the nucleotide; a CCD fluorescence detector and/or photomultiplier for detecting fluorescence induced by the laser; a data analysis device for analyzing data generated by the fluorescence detector; and an output device which reports the data analysis generated by the data analysis device.

Unlike certain prior art methods of detecting hybridization, no separation of the hybridization complexes from the uncomplexed probes is necessary in certain embodiments of the present method. In certain prior art methods, unhybridized probes and hybridized probes must be separated to enhance the signal to noise ratio (i.e., the ratio of the hybridization complex signal to the unhybridized probe signal or noise), enabling detection of hybridization. In the present separation-free method, the change in the overall signal is monitored without performing the additional burdensome step of separating the hybridized and unhybridized probes. The inventors have discovered that nucleotide sequence information, including information regarding nucleotide sequence concentration, can be determined by monitoring a change in the overall signal intensity, which is a function of hybridization and hybridization efficiency.

In particular, the inventors have discovered a signal quenching effect related to probe-nucleotide hybridization, wherein the intensity of laser induced fluorescence of an unbound probe exceeds that of the same probe bound to a nucleobase-containing sequence. Therefore, a solution lacking any target sequences for probes therein will fluoresce more intensely than an otherwise identical solution containing target sequences, and thus probe-nucleotide hybridization complexes.

Moreover, the intensity of laser induced fluorescence of hybridized probes is inversely proportional to the hybridization efficiency of the probes for their target sequences, in the separation-free embodiment of the invention. Therefore, a medium containing imperfectly complementary target sequences for probes therein will fluoresce more intensely than an otherwise identical medium containing perfectly complementary target sequences. A medium containing target sequences mismatching n bases of the probes therein will fluoresce more intensely than an otherwise identical medium containing target sequences mismatching less than n bases of the probes therein. Thus, a three mismatch medium fluoresces more intensely than a two mismatch medium, which fluoresces more intensely than a one mismatch medium, which fluoresces more intensely than a zero mismatch (completely complementary) medium.

The method of the invention can be used to determine whether an unacceptable concentration of a contaminant exists in a sample, wherein the contaminant is the target sequence for the antisense probes. The method can be used to determine whether the concentration of the contaminant exceeds a maximum allowable concentration of the contaminant in the sample, such as might be done for quality control purposes.

The precise concentration of the contaminant can be determined by reference to a calibration curve generated by positive controls. Alternatively, the fluorescent intensity of the test sample can be directly compared to a reference intensity of a positive control sample, which contains the contaminant at the maximum allowable concentration. The test sample and positive control samples can be tested concurrently or separately.

The intensities of the test sample and positive control sample can also be compared to a baseline intensity of a negative control sample substantially devoid of the contaminant. The negative control can be tested concurrently with the other samples, or separately.

In embodiments, the target sequence concentration determined by laser-induced fluorescence can be compared to the concentration of all nucleobase-containing sequences in the sample, as determined by, e.g., measuring the UV absorption at 260 nm. If the UV-derived concentration significantly exceeds the fluorescence-derived concentration, the sample may contain contaminants that absorb 260 nm UV light, such as contaminating nucleotide sequences. A significant difference is defined for present purposes as a difference not attributable to mere experimental variation.

Although solid supports and gels are not required to practice this invention, such supports can be used in embodiments of the invention to separate hybridized probes from unhybridized probes prior to measuring fluorescence, or for other purposes.

A plurality of probes can be employed simultaneously to achieve a variety of effects. Several probes targeted for different segments of a single nucleotide sequence can be employed to enhance the reliability of the method. Similarly, one probe can target one strand of dsDNA, while another probe can target the complementary strand of dsDNA. In embodiments, probes having different markers can be employed simultaneously. For example, one probe can have a fluorescein marker exhibiting a fluorescent emission intensity peak at 525 nm while the other probe can have a rhodamine marker exhibiting a fluorescent emission intensity peak at 580 nm.

The present invention makes it possible to limit the total volume of the liquid medium (i.e., the sample to be analyzed) in certain embodiments to about 5 microliters. Typically, the total volume is about 5 microliters to about 2000 microliters.

When the target sequence is dsDNA, if a result is obtained for which there remains doubt, a further test may be immediately performed on the sample by adding the complementary probe to test the complementary strand of DNA (at least when employing the PNA containing probes of the invention). Alternatively, the test can be done with both the probe and complementary probe hybridized to each of the denatured DNA strands in the first instance and at the same time.

For forensic applications, samples can be tested, stored and then retested, at least with PNA containing probes, because PNA is expelled from hybridization over a couple of days, and DNA recombines over time and does not degrade by this procedure. Accordingly, a sample frozen after testing can be subsequently retested in the same tube a number of times.

Clinical samples can be tested using at least 2000 times less chemicals or genomic material (5 microliters vs. 10 milliliters) than is typical in conventional methods. Therefore, even using 10 or 20 times the concentration of probe conventionally used, the tests still only consume ⅕th to ⅒th the amount of probe, while obtaining a very decisive result.

The invention will be illustrated in more detail with reference to the following Examples, but it should be understood that the present invention is not deemed to be limited thereto.

EXAMPLES

Target DNA synthesis

The following 150 bp DNA sequence from p53 wild type DNA (SEQ ID NO:1) was produced by a GeneAmp 2400 PCR system (Perkin Elmer) using conventional reagents and protocols specified by the manufacturer:

AACACCAGCT CCTCTCCCCA GCCAAAGAAG AAACCACTGG

ATGGAGAATA TTTCACCCTT CAGATCCGTG GGCGTGAGCG

CTTCGAGATG TTCC<u>GAGAGC</u> <u>TGAATGAGGC</u> CTTGGAACTC

AAGGATGCCC AGGCTGGGAA GGAGCCAGGG

Synthesis of Methylphosphonate Oligonucleotide Probes

The methylphosphonate oligonucleotide probes used in the examples were synthesized according to the conventional protocols specified by the manufacture of the DNA synthesizer employed for the synthesis (Expedite 8909, PerSeptive Biosystems). The coupling time for methyl phosphonamidites was six minutes. Methyl phosphonamidites (bz-dA-Me, ibu-dC-Me, ibu-dG-Me and dT-Me phosphonamidite) and fluorescent phosphoramidite were purchased from Glen Research (Sterling, Va.). Phosphoramidites and reagents for synthesis were purchased from PerSeptive Biosystems. Ethylenediamine (EDA), acetonitrile (ACN), ammonium hydroxide and ethyl alcohol (EtOH) were purchased from Sigma-Aldrich.

The deprotection procedures were based on the one-pot procedure disclosed by R. Hogrefe et al., Nucleic Acids Research, 1993, Vol. 21:2031–2039.

Partially methylphosphonated oligonucleotides were deprotected and cleaved by adding 1 ml of a mixture of EtOH/ACN/water/ammonium hydroxide (40/40/10/10 (V/V%)) to a CPG column along with the synthesized nucleotides, and driving the mixture back and forth through the column five times using a syringe. After thirty minutes at room temperature, 1 ml of EDA was added to the column, driven back and forth through the column five times, and then held at room temperature for six hours. The resulting solution was then collected from the column. The column was then washed twice using 1 ml of a 1:1 mixture of ACN and water, and the eluate was collected and added to the solution collected from the column prior to washing the column. This combined solution was then neutralized to pH 7 in an ice bath using 6 N HCl.

Completely methylphosphonated oligonucleotides were deprotected and cleaved by adding 1 ml of a mixture of EtOH/ACN/ammonium hydroxide (45/45/10 (V/V%)) to a CPG column along with the synthesized nucleotides, and driving the mixture back and forth through the column five times using a syringe. After thirty minutes at room temperature, 1 ml of EDA was added to the column, driven back and forth through the column five times, and then held at room temperature for six hours. The resulting solution was then collected from the column. The column was then washed twice using 1 ml of a 1:1 mixture of ACN and water, and the eluate was collected and added to the solution collected from the column prior to washing the column. This combined solution was then neutralized to pH 7 in an ice bath using 6 N HCl containing 10% acetonitrile (V/V%).

After deprotection, the oligonucleotides were purified by reverse-phase HPLC, using a 7.8×300 mm Delta Pak C18 column (Waters, Milford, Mass.). The solvents were 0.1 M triethylammonium acetate (TEAA), pH 7, and a mixture of ACN and water (95:5 (V:V)) The gradient was from 10 to 40% (Vol.% TEAA in ACN/Water) over 30 minutes. The flow rate was 4 ml/minute.

Collected fractions having the desired purity were pooled and lyophilized with ACN/water (1:1) three times to remove TEAA. The resulting dried pellets were soluble in water (if partially methylphosphonated) or in a 20/80% mixture of ACN/water (if completely methylphosphonated).

The following anionic 18mer modified backbone DNA probe with 4 methylated groups was employed in Examples 1A–1F:

5' Fluo-C CTmC ATTm CAG CmTC TCmG GA 3'(SEQ ID NO:2)

Probe/Target Hybridization

Examples 1A–1F

In each of Examples 1A–1F, a 200 microliter sample was prepared by mixing targets (150 bp DNA sequence from p53 wild type DNA (SEQ ID NO:1)), probes (5' Fluo-C CTmC ATTm CAG CmTC TCmG GA 3' (SEQ ID NO:2)),0.5×TBE buffer and/or TE buffer in the following amounts:

| Example | 1A | 1B | 1C | 1D | 1E | 1F |
|---|---|---|---|---|---|---|
| Target | 27.5 | 20.3 | 13.7 | 6.9 | 3.3 | 0 |
| (pmols) | (50 μl) | (37 μl) | (25 μl) | (12.5 μl) | (6 μl) | |
| Probe | 100 | 100 | 100 | 100 | 100 | 100 |
| (pmols) | (10 μl) | (10 μl) | (10 μl) | (10 μl) | (10 μl) | (10 μl) |
| 0.5×TBE Buffer | 50 μl | 50 μl | 50 μl | 50 μl | 50 μl | 50 μl |
| TE Buffer | 0 | 13 μl | 25 μl | 37.5 μl | 37.5 μl | 50 μl |

Each sample was heated at 95° C. for 8 minutes. Then, the samples were left to hybridize at room temperature for 30 minutes. Each sample was separated by G50 spin column (Pharmacia Biotech, Uppsala, Sweden) by spinning at 950 rpm for 3 minutes. The solution containing the hybridization complexes passed through the column and was transferred into a cuvette for fluorescent detection using the protocols disclosed in our prior U.S. patent application Ser. Nos. 08/807,901, 08/870,370 and 08/886,280. The fluorescent spectra were recorded at a 2048 ms integrating time.

Figure 2:
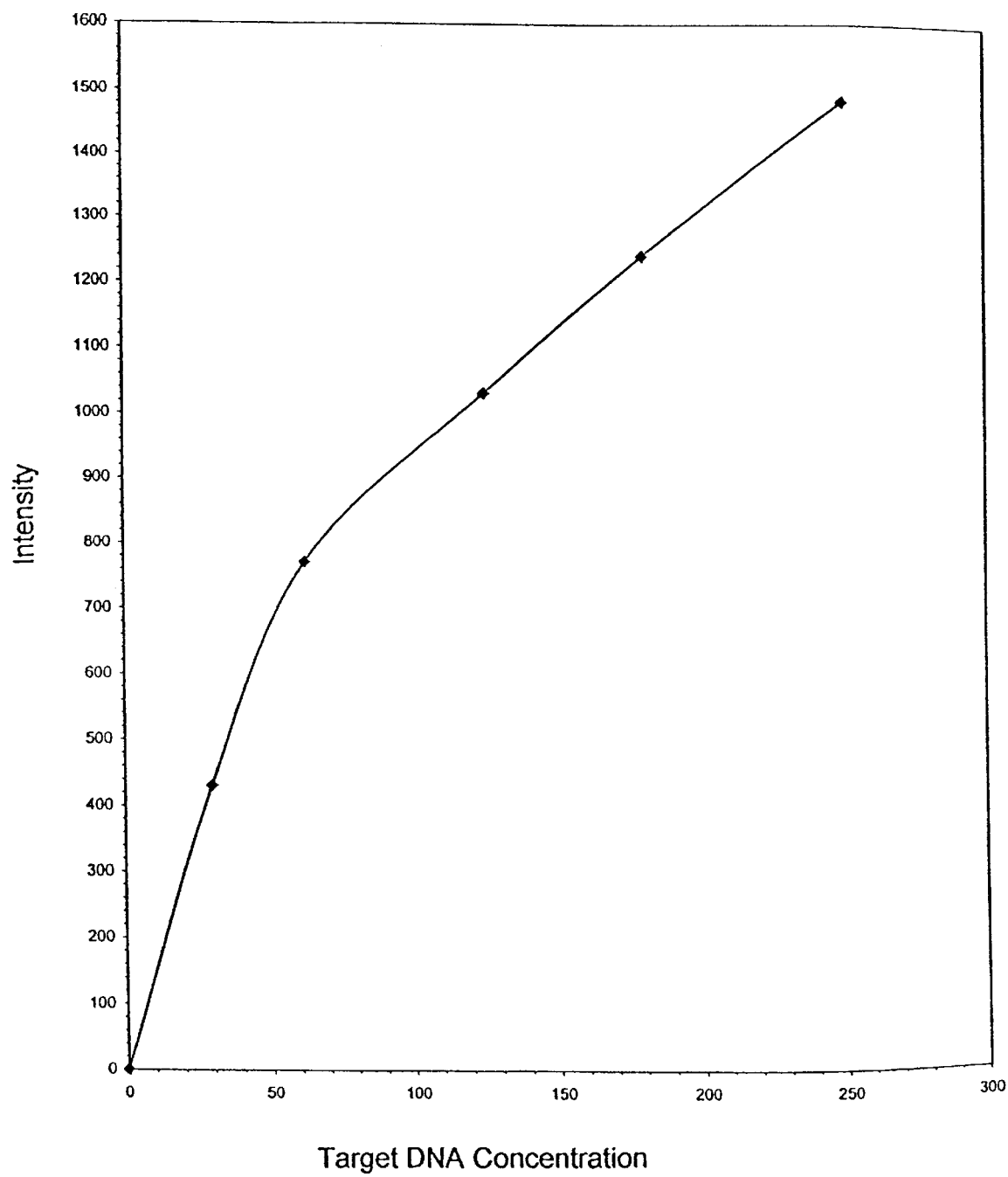
FIG. 2 shows a calibration curve generated from the spectral data shown in FIG. 1.

The detection results are shown in FIG. 1, with the spectrum of negative control Example 1F used as a baseline and substracted from the other spectra. FIGS. 1 and 2 demonstrate that fluorescent intensity increases along with increasing target DNA concentration. The calibration curve of FIG. 2 can be used to predict the concentration of target in samples containing unknown quantities of the target.

Examples 2A–2H

In each of Examples 2A–2H, a 120 microliter sample was prepared by mixing targets (150 bp DNA sequence from p53 wild type DNA (SEQ ID NO:1)), PNA probe, 0.5×TBE buffer (pH 6.5) and/or TE buffer (pH 8.0) in the following amounts:

| Example | 2A | 2B | 2C | 2D | 2E | 2F | 2G | 2H |
|---|---|---|---|---|---|---|---|---|
| Target | | | | | | | | |
| (pmols) | 0 | 1.2 | 2.4 | 4.8 | 9.6 | 11.5 | 15.4 | 19.2 |
| (μl) | 0 | 3 | 6 | 12.5 | 25 | 30 | 40 | 50 |
| Probe | | | | | | | | |
| (pmols) | 20 | 20 | 20 | 20 | 20 | 20 | 20 | 20 |
| (μl) | 10 | 10 | 10 | 10 | 10 | 10 | 10 | 10 |
| 0.5×TBE Buffer | 60 μl | 60 μl | 60 μl | 60 μl | 60 μl | 60 μl | 60 μl | 60 μl |
| TE Buffer | 50 μl | 47 μl | 44 μl | 37.5 μl | 25 μl | 20 μl | 10 μl | 0 μl |

The PNA probe used in Examples 2A–2H was obtained from PerSeptive Biosystems, and had the following sequence:

H-Fluo-linker-CTC ATT CAG CTC TCG-Lys-CONH$_2$.

Each sample was heated at 95° C. for 5 minutes. Then, the samples were left to hybridize at room temperature for 30 minutes. Each sample was transferred to a cuvette (without separating hybridization complexes from unhybridized probes) for fluorescent detection using the protocols disclosed in our prior U.S. patent applications Ser. Nos. 08/807,901, 08/870,370 and 08/886,280. The fluorescent spectra were recorded at a 2048 ms integrating time.

Figure 3:
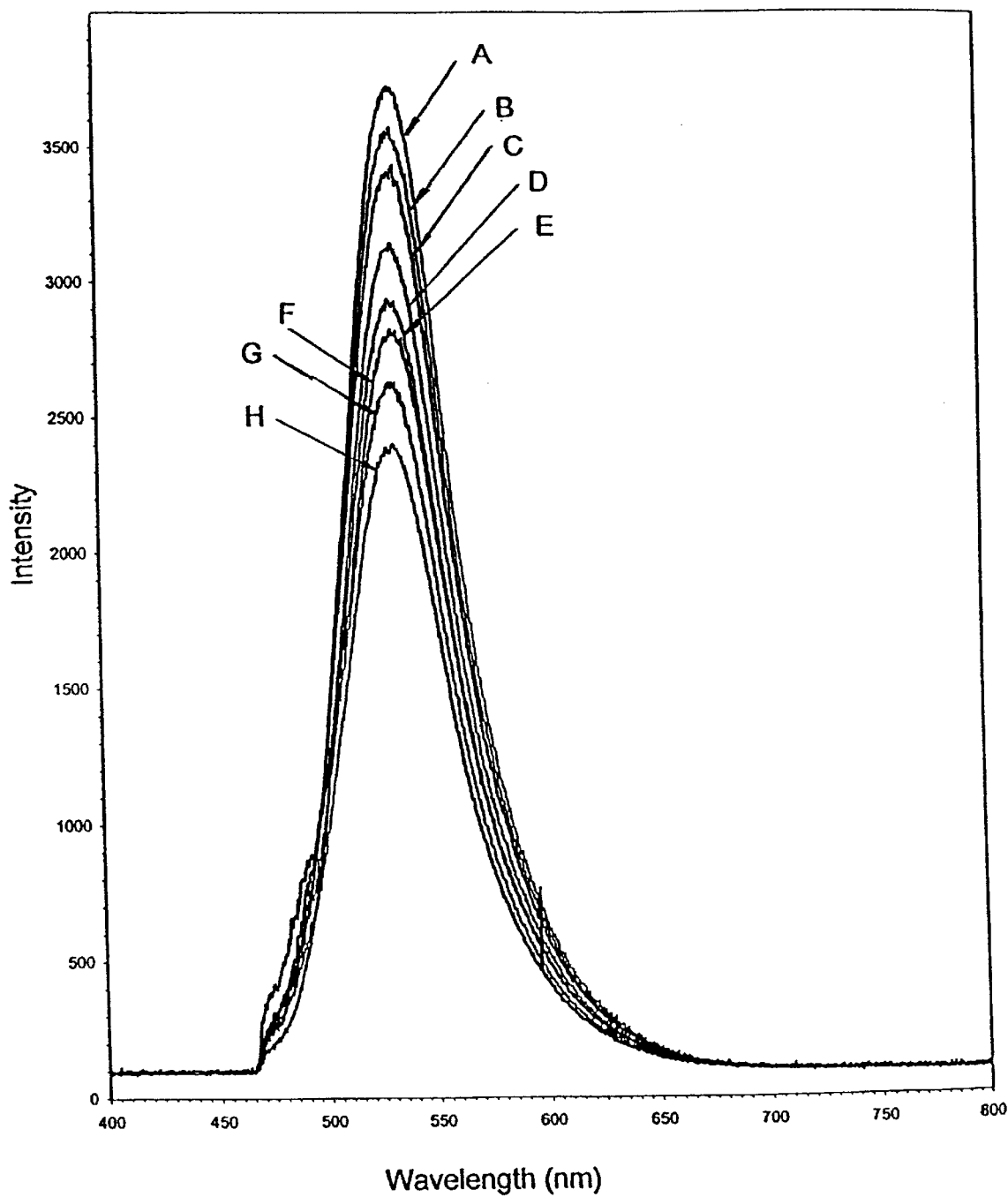
FIG. 3 shows the fluorescent quenching spectra produced by a series of samples having increasing concentrations of a target nucleotide sequence.
Figure 4:
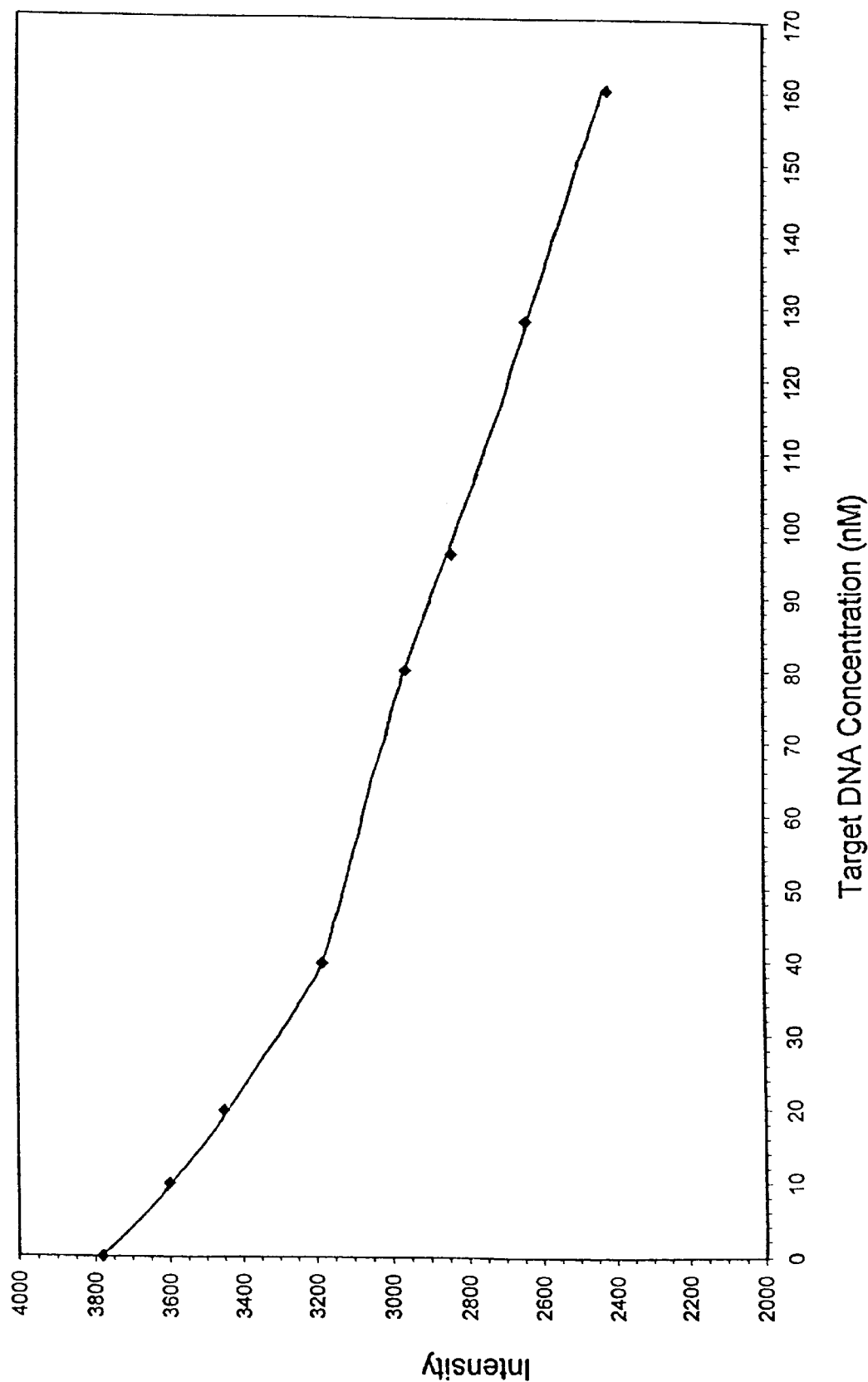
FIG. 4 shows a calibration curve generated from the spectral data shown in FIG. 3.

The results are shown in FIGS. 3 and 4, which demonstrate that fluorescent intensity decreases with increasing target DNA concentration. The calibration curve of FIG. 4 can be used to predict the concentration of target in samples containing unknown quantities of the target.

While the invention has been described in detail and with reference to specific examples thereof, it will be apparent to one skilled in the art that various changes and modifications can be made therein without departing from the spirit and scope thereof.

What is claimed is:

1. A method for determining a concentration of at least one single stranded or double stranded nucleobase-containing target sequence in a fluid medium, said method comprising:
   adding to said fluid medium antisense probes capable of forming hybridization complexes with said at least one nucleobase-containing target sequence, wherein said antisense probes comprise fluorescent markers and backbones having a charge that is less negative than a comparable phosphodiester backbone;
   separating unhybridized antisense probes from said hybridization complexes to form a test medium;
   irradiating said test medium with a laser beam having a wavelength which excites fluorescent markers in said hybridization complexes and causes said fluorescent markers to emit fluorescent light;
   measuring an intensity of said emitted fluorescent light; and
   comparing said measured intensity with a reference intensity to determine a concentration of said at least one target sequence in said fluid medium,
   wherein said measured intensity is proportional to said concentration, and wherein said method other than said separating step is entirely conducted without binding said antisense probes, said at least one nucleobase-containing target sequence or said hybridization complexes to a solid support or gel.

2. The method of claim 1, wherein said backbones comprise at least one uncharged linking group between a 5' carbon and a 3' carbon of adjacent sugars.

3. The method of claim 2, wherein said at least one uncharged linking group is a methylphosphonate group.

4. The method of claim 1, wherein said backbone comprises a modified phosphodiester backbone having at least about 10% of its phosphate groups replaced with uncharged groups.

5. The method of claim 4, wherein said uncharged groups are methylphosphonate groups.

6. The method of claim 1, wherein said backbone comprises a modified phosphodiester backbone having at least about 20% and not more than about 80% of its phosphate groups replaced with uncharged groups.

7. The method of claim 6, wherein said uncharged groups are methylphosphonate groups.

8. The method of claim 1, wherein said backbone comprises a modified phosphodiester backbone having about 25% of its phosphate groups replaced with uncharged groups.

9. The method of claim 7, wherein said uncharged groups are methylphosphonate groups.

10. The method of claim 1, wherein said backbone comprises a modified phosphodiester backbone having about 50% of its phosphate groups replaced with uncharged groups.

11. The method of claim 10, wherein said uncharged groups are methylphosphonate groups.

12. The method of claim 1, wherein said backbone comprises at least one peptide nucleic acid segment and at least one phosphodiester segment.

13. The method of claim 12, wherein said backbone further comprises at least one methylphosphonate segment.

14. The method of claim 1, wherein said at least one target sequence is a contaminant in said fluid medium, and said method determines whether said concentration of said contaminant exceeds a maximum allowable concentration of said contaminant in said fluid medium.

15. The method of claim 14, wherein said reference intensity is an intensity of a positive control detected concurrently with said measured intensity, said positive control comprising said contaminant at said maximum allowable concentration.

16. The method of claim 15, wherein said reference intensity and said measured intensity are compared with a baseline intensity of a negative control detected concurrently with said reference and measured intensities, said negative control being substantially devoid of said contaminant.

17. A method for determining a concentration of at least one single stranded or double stranded nucleobase-containing target sequence in a fluid medium, said method comprising:
  adding to said fluid medium antisense probes capable of forming a hybridization complex with said at least one nucleobase-containing target sequence, wherein said antisense probes comprise fluorescent markers and backbones having a charge that is less negative than a comparable phosphodiester backbone;
  irradiating said fluid medium with a laser beam having a wavelength which excites fluorescent markers in said hybridization complex and causes said fluorescent markers to emit fluorescent light;
  measuring an intensity of said emitted fluorescent light; and
  comparing said measured intensity with a reference intensity to detect whether said fluid medium contains said at least one target sequence,
  wherein said measured intensity is inversely proportional to said concentration, and said method is conducted without separating unhybridized probes from hybridization complexes prior to said signal detecting, and without providing a signal quenching agent on said antisense probes or on said at least one nucleobase-containing target sequence.

18. The method of claim 17, wherein said backbones comprise at least one uncharged linking group between a 5' carbon and a 3' carbon of adjacent sugars.

19. The method of claim 17, wherein said at least one uncharged linking group is a methylphosphonate group.

20. The method of claim 17, wherein said backbone comprises a modified phosphodiester backbone having at least about 10% of its phosphate groups replaced with uncharged groups.

21. The method of claim 20, wherein said uncharged groups are methylphosphonate groups.

22. The method of claim 17, wherein said backbone comprises a modified phosphodiester backbone having at least about 20% and not more than about 80% of its phosphate groups replaced with uncharged groups.

23. The method of claim 22, wherein said uncharged groups are methylphosphonate groups.

24. The method of claim 17, wherein said backbone comprises a modified phosphodiester backbone having about 25% of its phosphate groups replaced with uncharged groups.

25. The method of claim 24, wherein said uncharged groups are methylphosphonate groups.

26. The method of claim 17, wherein said backbone comprises a modified phosphodiester backbone having about 50% of its phosphate groups replaced with uncharged groups.

27. The method of claim 26, wherein said uncharged groups are methylphosphonate groups.

28. The method of claim 17, wherein said backbone comprises at least one peptide nucleic acid segment and at least one phosphodiester segment.

29. The method of claim 28, wherein said backbone further comprises at least one methylphosphonate segment.

30. The method of claim 17, wherein said at least one target sequence is a contaminant in said fluid medium, and said method determines whether said concentration of said contaminant exceeds a maximum allowable concentration of said contaminant in said fluid medium.

31. The method of claim 30, wherein said reference intensity is an intensity of a positive control detected concurrently with said measured intensity, said positive control comprising said contaminant at said maximum allowable concentration.

32. The method of claim 31, wherein said reference intensity and said measured intensity are compared with a baseline intensity of a negative control detected concurrently with said reference and measured intensities, said negative control being substantially devoid of said contaminant.

* * * * *